US00PP08559P

United States Patent [19]

Okudai et al.

[11] Patent Number: Plant 8,559

[45] Date of Patent: Jan. 25, 1994

[54] CITRUS TREE "TSUNOKAORI"

[75] Inventors: Naomi Okudai, Isahaya; Iwao Oiyama, deceased, late of Kure, by Kazuko Oiyama, legal representative; Ryoji Matsumoto, Chikushino; Toshio Takahara, Nago; Denji Ishiuchi, Age; Kensuke Asada, Omura; Masashi Yamamoto, Minamitakaki; Hirono Murata, Minamitsugaru, all of Japan

[73] Assignee: Fruit Tree Research Station Ministry of Agriculture, Forestry and Fisheries, Tsukuba, Japan

[21] Appl. No.: 840,073

[22] Filed: Feb. 25, 1992

[51] Int. Cl.[5] ..... A01H 5/00

[52] U.S. Cl. ..... Plt./45

[58] Field of Search ..... Plt. 45

*Primary Examiner*—James R. Feyrer

*Attorney, Agent, or Firm*—Armstrong, Westerman, Hattori, McLeland & Naughton

[57] ABSTRACT

Disclosed is a citrus tree having a moderate spreading vigor, and bearing medium size and rounded fruit with an orange skin color. This new and distinct variety of citrus tree is a late maturing citrus cultivar, is bred by a crossing of "Kiyomi" (the seed parent) and "Okitsu-wase" (the pollen parent), *Citrus unshiu*, bears good quality fruit, and is an excellent citrus cultivar.

6 Drawing Sheets

BACKGROUND OF THE VARIETY

The present invention relates to a new and distinct variety of citrus tree, and more particularly, to a citrus tree having a moderate vigor and bearing an excellent table fruit.

In Japan, presently "Kawano Natsudaidai" (*C. natsudaidai*) and "Hassaku" (*C. hassaku*), which are mid- to late-maturing cultivars, are the main widely cultivated citrus varieties, even though their fruit have many seeds and a hard peeling characteristics, and their flesh is of low eating quality.

The breeding by the present breeders have been aimed at obtaining a new variety that can replace "Kawano Natsudadai" and "Hassaku". Namely, the object of the invention is to provide a new and distinct variety of citrus tree bearing a fruit with a better taste and appearance than "Hassaku", etc., and seedlessness, the fruit ripening in mid-to late-season.

In comparison to the above-mentioned varieties, the fruit of the present new variety has a high sweetness (i.e., high Brix) with a moderate sub-acidity level, coupled with a general absence of seeds which makes the fruit highly suitable as a table fruit. The fruit of the present new variety is also easier to peel. Its skin is thin and smooth. The fruit is juicy and the flesh is soft and has a flavor similar to that of an orange.

ORIGIN AND ASEXUAL REPRODUCTION OF THE VARIETY

This new variety of citrus tree was a cross-seedling obtained from a crossing of "Kiyomi" (♀) (the seed parent) and "Okitsu-Wase" (♂) (the pollen parent) at the Kuchinotsu Branch, Fruit Tree Research Station (Otsu-870, Kuchinotsu-cho, Minamitakaki-gun, Nagasaki-ken, Japan).

Specifically, this crossing was carried out at the Kuchinotsu Branch in 1972, and in 1973 the resulting seeds were sown in a breeding field to grow seedlings. The seedlings obtained were top-worked to a *Citrus unshiu* Marc. for interstock, to shorten juvenile phase, in September, 1974, and the trees thus-grown started bearing in 1978, and were selected based on the good appearance and quality of the fruit of the trees. The trees were given a strain name "Kuchinotsu 12", and then tests for regional adaptability and of specific character were conducted at several research stations from 1984 to 1990. As a result, it was found that the trees had stable characteristics, and can be distinguished from other similar varieties. The breeders denominated the aforesaid citrus variety of tree in accordance with this invention as "Tsunokaori". The genus of the cultivar is "Citrus", and the group of the same is "tangor".

The aforesaid variety "Kiyomi" is the seed parent and is a late maturing citrus that always provides a monoembryony cross seedling, and bears fruit with a soft and juicy flesh and a good taste. Another variety "Okitsu-Wase" is an early maturing citrus, and bears fruit that are easily peeled and have a thin segment membrane for an easy eating thereof.

The breeders asexually reproduced this new and distinct variety of citrus tree "Tsunokaori", by grafting, at the Kuchinotsu Branch, Okitsu Branch, and Akitsu Branch of the Fruit Tree Research Station, Ministry of Agriculture, Forestry and Fisheries, Japan, and confirmed the homogeneity and stability of "Tsunokaori" according to this invention.

An application for this new variety of citrus tree "Tsunokaori" under the Seeds and Seedlings Law of Japan was filed on Mar. 31, 1991, under the filing number 3821.

SUMMARY OF THE VARIETY

This new variety of citrus tree has a moderate vigor with growth habit of spreading, and the shoots of same have an internode with a moderate thickness and length, and have a high density. There are no thorns on the tree, and the shape of the leaf of the tree is fusiform and mainly wavy, similar in appearance to "Kiyomi". The size of the leaf is smaller than that of "Kiyomi", and is slightly smaller than that of "Okitsu-Wase". The flower is solitary, and is smaller than that of "Okitsu-Wase" but is the same size as that of "Kiyomi". The color of the flower is white (JHSC 2902), corresponding to yellowish white in the ISCC-NBS system, and it has 4 petals. This variety is dipoloid, as are both of its parents. The tree has pollen of male sterility and has a parthenocarpic bearing habit. While the variety is commercially regarded as seedless, a seed may be found in rare instances in its fruit. Such seed, when examined, has been found to contain a polyembryo resulting from cross-pollination. The bearing age and fruit set percentage of the tree are medium.

Although the fruit generally has a size of about 160 g, the trees bear over 200 g fruit with Brix decreased by defloration. The shape of the fruit is rounded and squat, wider than it is tall, with both the base and apex being flattened, and oblate. The skin of the fruit has a deeper orange-color than that of "Kiyomi", and the optimum color of the fruits is reached in mid-December. The surface of the fruit is smooth and the skin is thin, and is easily peeled although the peeling characteristic is inferior to that of a usual *Citrus unshiu*. The fruit have no peel puffing, and the flesh is also orange-colored. Although the texture of the flesh is slightly inferior to that of "Kiyomi", the flesh is soft and juicy and has the same orange flavor as "Kiyomi". Further, the flesh has a high Brix and a good taste. The segment membranes are thin, the content of citric acid in the flesh starts to decrease at a later date, and the ripening time of the fruit appears to be in late March to mid-April, i.e., it is a late maturing variety. The embryo is white (JHSC 2702, corresponding to pale yellow in the ISCC-NBS system) colored, and is a polyembryo. The fruit can be kept for a long time.

Regarding damage by disease, the tree of this invention has a strong resistance to scab, but a weak resistance to bacterial canker. There is little occurrence of stem pitting.

Further, the tree of this variety requires overwintering of the fruit on-tree, and thus the tree is preferably cultured in a frost free area during winter.

The color values presented herein are taken from the Japanese Horticultural Plant Standard Color Chart (JHSC) with cross-reference to the ISCC-NBS system.

DESCRIPTION OF THE VARIETY

Figure 1:
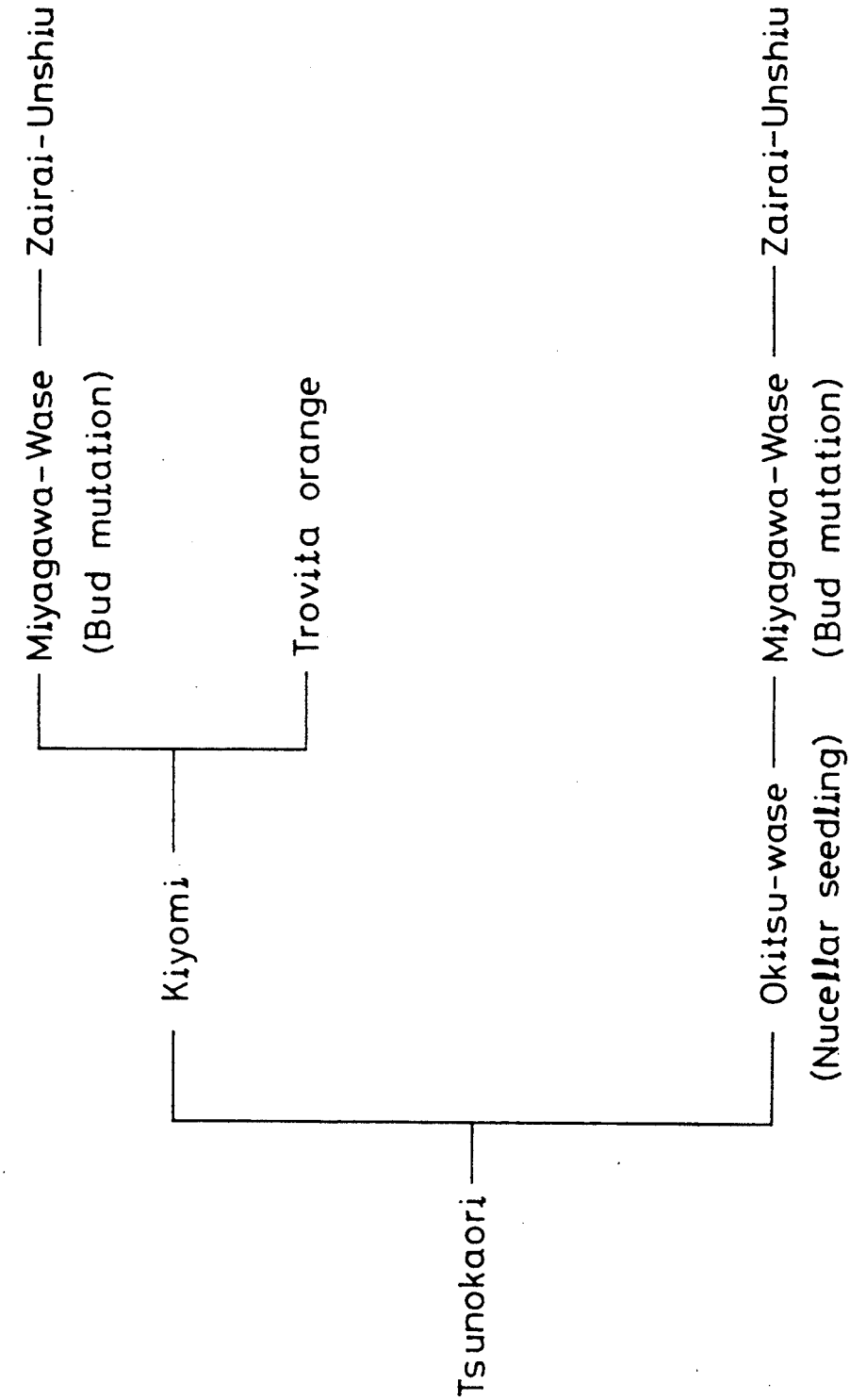
FIG. 1 gives the pedigree of the new and distinct variety of the citrus tree "Tsunokaori"
Figure 2:
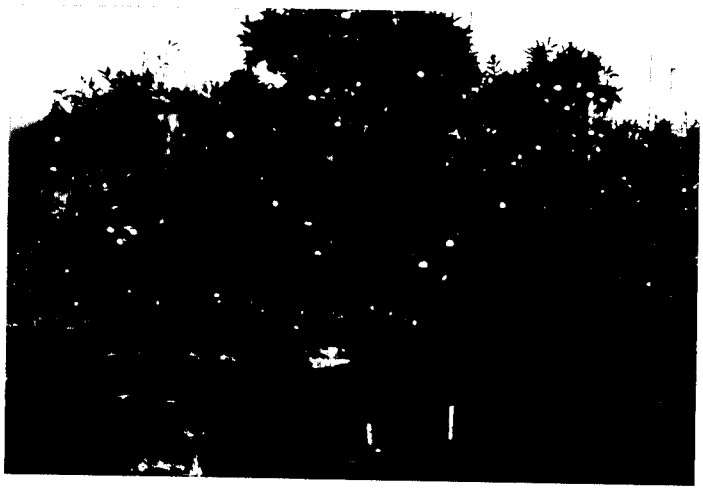
FIG. 2 is a photograph of a shape of the new variety of citrus tree.
Figure 3:
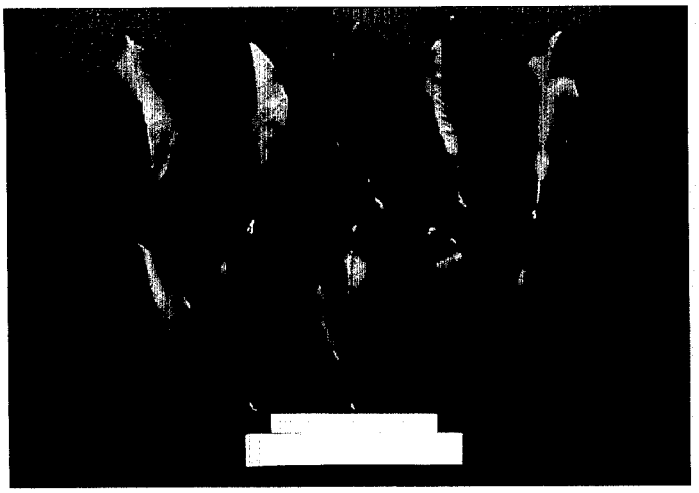
FIG. 3 is a photograph of adult leaves (upper and reverse side) of the new variety of citrus tree.
Figure 4:
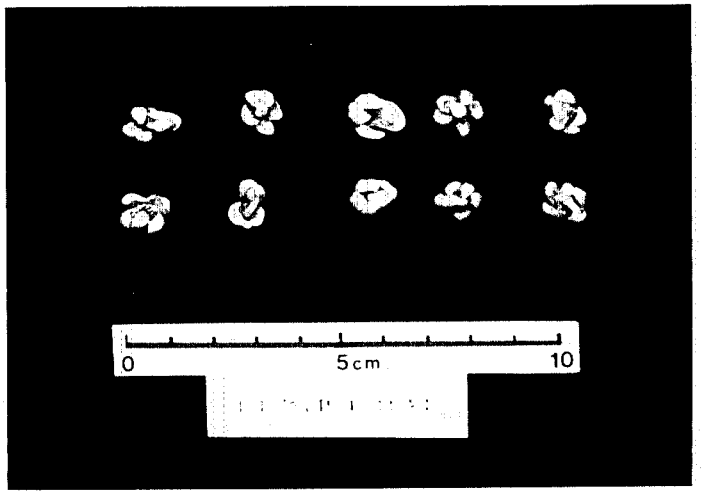
FIG. 4 is a photograph of the flowers of the new variety of citrus tree.
Figure 5:
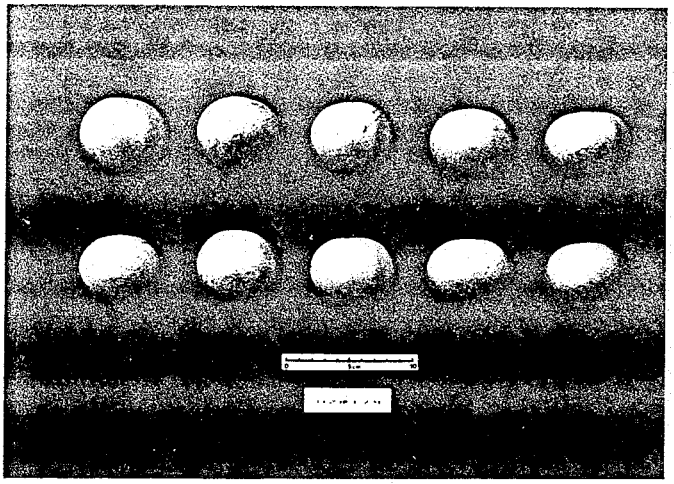
FIG. 5 is a photograph of side views of the fruit of the new variety of citrus tree.
Figure 6:
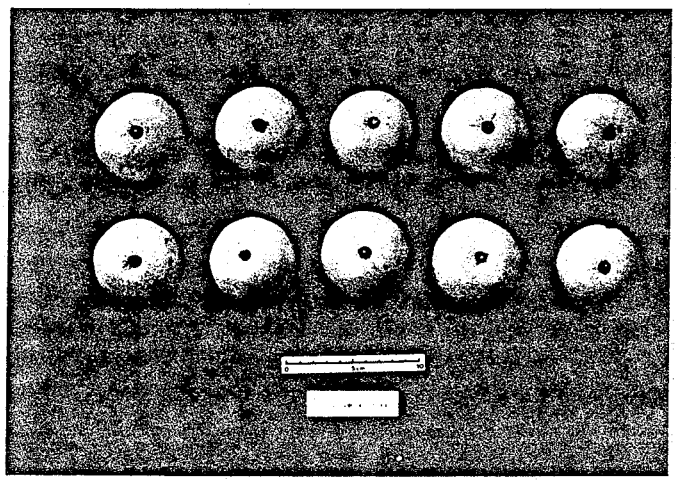
FIG. 6 is a photograph of stylar end of the fruit of the new variety of citrus tree.
Figure 7:
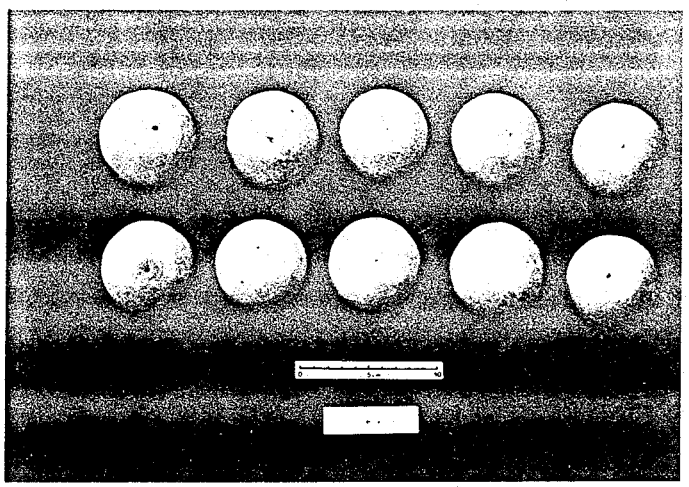
FIG. 7 is a photograph of basal end of the fruit of the new variety of citrus tree.
Figure 8:
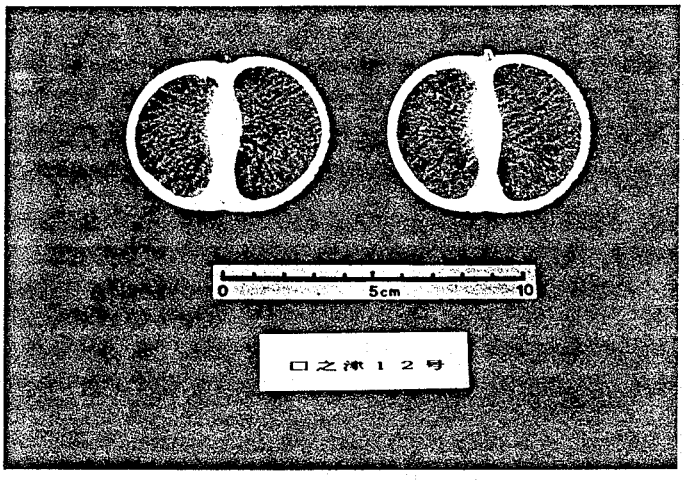
FIG. 8 is a photograph of longitudinal-sectional views of the fruit of the new variety of citrus tree.
Figure 9:
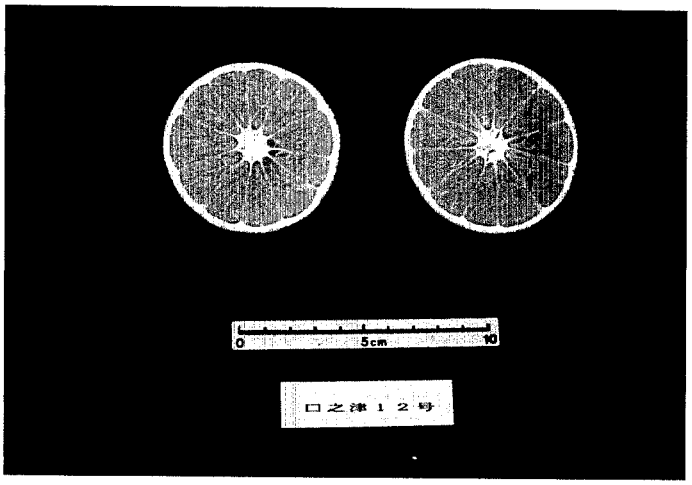
FIG. 9 is a photograph of cross-sectional views of the fruit of the new variety of citrus tree.

The characteristics of the new and distinct variety of citrus tree "Tsunokaori" are as follows:

Tree and branch:

*Habit of branches.*—Spreading.

*Mean angle of scaffold branches to trunk based on* 10 branches.—59.0° (range from 35° to 75°).

*Size of tree.*—Medium. An average tree which is grafted on a rootstock (*C. trifoliata*) and is 11 years old has a width of 2.2 m and a height of 2.2 m, based on average of 3 trees.

*Vigor.*—Medium. The trunk circumference of a typical tree is 9.7 cm in its fourth year of growth; and 12.3 cm in its fifth year. The vigor of the tree is therefore 127% of the vigor of trees in six growing districts in Japan.

*Thickness of shoot.*—Medium. The typical internode length is 15.6 mm, based on an average of 10 branches, the range being from 11 mm to 23 mm.

*Length of internode.*—Medium

*Number of prickles on shoot.*—None (All of the above characteristics of the variety are similar to those of "Kiyomi" (K) and "Okitsu-Wase" (O))

Leaf:

*Leaf shape.*—Generally spindle-shaped, base and apex acute. Leaf margins are repand.

*Leaf blade shape index.*—Medium, 44.8% (K: 43.0%, O: 41.1%).

*Angle of leaf blade apex.*—Sharp, 71.1° (K: 56.8°, O: 57.1°).

*Angle of leaf blade base.*—Moderate, 70.8° (K: 63.9°, O, 62.9°).

*Undulation of leaf blade.*—Strong, same as "K".

*Thickness of leaf blade.*—Thin, 0.24 mm (K: 0.3 mm, O: 0.29 mm).

*Area of leaf blade.*—Small, 28.4 $cm^2$ (K: 30.2 $cm^2$, O: 29.3 $cm^2$).

*Length of leaf blade.*—Short, 9.7 cm (K: 10.1 cm., O: 10.3 cm).

*Width of leaf blade.*—Medium, same as "K" and "O".

*Sharpness of vein.*—Unclear, same as "K" and "O".

*Shape of wings.*—None, same as "K" and "O"

*Length of petiole.*—Medium, 1.9 cm (K: 1.6 cm, O: 1.7 cm).

Rate of petiole.—Large, 19.6% (K: 15.8%, O: 16.5%).

Flower:

*Formation of inflorescence.*—Solitary, same as "O".

*Weight of flower bud.*—light, 0.25 g (K: 0.27 g, O: 0.60 g).

*Shape of petal apex.*—Sharp.

*Shape of petal base.*—Straight.

*Length of petal.*—Short, 9.8 mm (K: 12.2 mm, O: 19.3 mm).

*Color of petal.*—White (JHSC 2902), same as "K" and "O".

*Number of petals.*—Few, 3.5 (K: 4.3, O: 5.0).

*Degree of separation of filament.*—Separative, same as "K" and "O".

*Fertility of pollen.*—Sterile, same as "K" and "O".

*Size of ovary.*—Large, 3.8 mm in diameter (K: 3.2 mm, O: 4.1 mm).

Fruit:

*Shape of fruit.*—Round, same as "K" and "O".

*Size of fruit.*—Average height of 4.6 cm and width of 6.1 cm. Good uniformity in size of fruit.

*Rate of flat area of fruit stylar end to fruit breadth, in diameter.*—Small, 35% (K: 34.5%, O: 37.7%).

*Depth of navel.*—Shallow, same as "K" and "O".

*Size of stylar scar.*—Small, 2.3 mm (K: 3.9 mm, O: 2.3 mm).

*Rate of flat area of basal end to fruit breadth, in diameter.*—Large, 37.6% (K: 32.0%, O: 31.1%).

*Number of radially corrugated fruit on peduncle.*—None, same as "K" and "O".

*Size of columella in cross section.*—Small, 3.4% (K: 3.2%, O: 5.6%).

*Size of fruit.*—Medium, 142 g (K: 178 g, O: 102 g).

*Color of overskin.*—Orange (JHSC 1605), corresponding to vivid orange in ISCC-NBS system.

*Size of oil glands.*—Large, slightly larger than "O".

*Type of skin surface.*—Smooth, same as "K" and "O".

*Density of oil glands.*—Dense, 56 oil. glands/$cm^2$ (K: 34 o.g./$cm^2$, O: 25 o.g./$cm^2$).

*Irregularity of oil glands.*—Flat, same as "O".

*Number of dents.*—None.

*Thickness of peel.*—Thin, 2.8 mm (K: 3.7 mm, O: 2.7 mm).

*Hardness of peeling.*—Moderate, same as "K".

*Touchness of segment membrane.*—Soft, same as "K" and "O".

*Shape of juice sac.*—Spindle-shape.

*Size of juice sac.*—Small.

*Color of juice sac.*—Orange (JHSC 1306), corresponding to vivid orange in ISCC-NBS system.

*Juice amount.*—Very juicy.

*Sweetness.*—Rich (Brix 13.9° to 15.0°).

*Acidity.*—Moderate.

*Number of seed.*—Rare.

*Color of embryo.*—White (JHSC 2702), corresponding to pale yellow in ISCC-NBS system.

*Number of embryo.*—Polyembryony.

*Germination of time.*—Medium, March 21st (K: March 14th, O: March 14th).

*Flowering time.*—Medium, May 2nd (K: April 28th, O: April 28th).

*Time of maturity of fruit*.*—Late (April 1st to 10th).

*in the Nagasaki prefecture district, Japan.

*Alternate bearing.*—Medium.

*Physiological characteristics.*—Occurrence of sunburn: Very little. Occurrence of peel puffing: Very little. Occurrence of fruit cracking: Very little. Resistance to disease: Strong. Resistance to pest: Moderate.

*On-tree storability.*—Low to moderate on the tree. The fruit exhibits cracking on the skin at the stem end, flesh granulation occurs, and thus regreening of the skin does not occur. Rather, the skin color (orange) fades.

*Storability after picking.*—Good.

We claim:

1. A new and distinct variety of citrus tree, substantially as illustrated and described herein, characterized over known citrus trees by (A) having a moderate vigor with a spreading growth habit; (B) having a medium round fruit, with an orange skin color, and a smooth and thin skin;

wherein said fruit is easily peeled; and the flesh of the fruit has a soft texture and a moderate orange flavor, is juicy and sweet; and has a good keeping quality; and thus said fruit is suitable as table fruit; and (C) belonging to a late maturing citrus variety.

* * * * *

Pedigree of 'Tsunokaori'